United States Patent
Park et al.

(10) Patent No.: US 12,427,143 B2
(45) Date of Patent: Sep. 30, 2025

(54) PHARMACEUTICAL COMPOSITION FOR TREATING OR PREVENTING AGING OR AGE-RELATED DISEASES

(71) Applicants: INU RESEARCH & BUSINESS FOUNDATION, Incheon (KR); KOREA UNIVERSITY RESEARCH AND BUSINESS FOUNDATION, SEJONG CAMPUS, Sejong-si (KR)

(72) Inventors: Joon Tae Park, Incheon (KR); Yun Haeng Lee, Seoul (KR); Young Joo Byun, Daejeon (KR); Do Young Choi, Seoul (KR)

(73) Assignees: INU RESEARCH & BUSINESS FOUNDATION, Incheon (KR); KOREA UNIVERSITY RESEARCH AND BUSINESS FOUNDATION, SEJONG CAMPUS, Sejong-si (KR)

( * ) Notice: Subject to any disclaimer, the term of this patent is extended or adjusted under 35 U.S.C. 154(b) by 908 days.

(21) Appl. No.: 17/633,576

(22) PCT Filed: Jul. 23, 2021

(86) PCT No.: PCT/KR2021/009592
§ 371 (c)(1),
(2) Date: Feb. 7, 2022

(87) PCT Pub. No.: WO2022/177075
PCT Pub. Date: Aug. 25, 2022

(65) Prior Publication Data
US 2023/0158014 A1  May 25, 2023

(30) Foreign Application Priority Data
Feb. 18, 2021  (KR) .................. 10-2021-0022067

(51) Int. Cl.
*A61K 31/4745* (2006.01)
*A23L 33/10* (2016.01)
*A61K 8/49* (2006.01)
*A61Q 19/08* (2006.01)

(52) U.S. Cl.
CPC .......... *A61K 31/4745* (2013.01); *A23L 33/10* (2016.08); *A61K 8/49* (2013.01); *A61Q 19/08* (2013.01)

(58) Field of Classification Search
None
See application file for complete search history.

(56) References Cited

U.S. PATENT DOCUMENTS

| | | |
|---|---|---|
| 5,182,290 A | 1/1993 | Albaugh |
| 2020/0121634 A1 | 4/2020 | Lee et al. |

FOREIGN PATENT DOCUMENTS

| | | | |
|---|---|---|---|
| CN | 110201173 A | 9/2019 | |
| KR | 10-2015-0025520 A | 3/2015 | |
| KR | 10-2016-0131253 A | 11/2016 | |
| KR | 10-1839721 B1 | 3/2018 | |
| KR | 10-2020-0004752 A | 1/2020 | |
| KR | 10-2203703 B1 | 1/2021 | |
| WO | WO-2020009374 A1 * | 1/2020 | ......... A61K 31/4738 |

OTHER PUBLICATIONS

International Search Report for PCT/KR2021/009592 mailed Nov. 11, 2021 from Korean Intellectual Property Office.

* cited by examiner

Primary Examiner — Kortney L. Klinkel
Assistant Examiner — Donna M Nestor
(74) Attorney, Agent, or Firm — Revolution IP, PLLC

(57) ABSTRACT

HTS screening was performed regarding cell proliferation, one of symptoms of senescence. As a result, KB1541, which was the most effective on cell proliferation, was earned. The present invention described how the compound regulates cell proliferation and senescence. The present invention uncovered what proteins interacted with the compound using streptavidin-magnetic beads after treating with biotin-connected KB1541. Consequently, it was identified that mitochondrial proteins interacted with the compound. In ATP assay, electron microscope and IP assay, the inventors identified that the compound regulated mitochondrial proteins and thereby increased ATP production as well as recovered senescence.

8 Claims, 7 Drawing Sheets

Specification includes a Sequence Listing.

[FIG. 1]
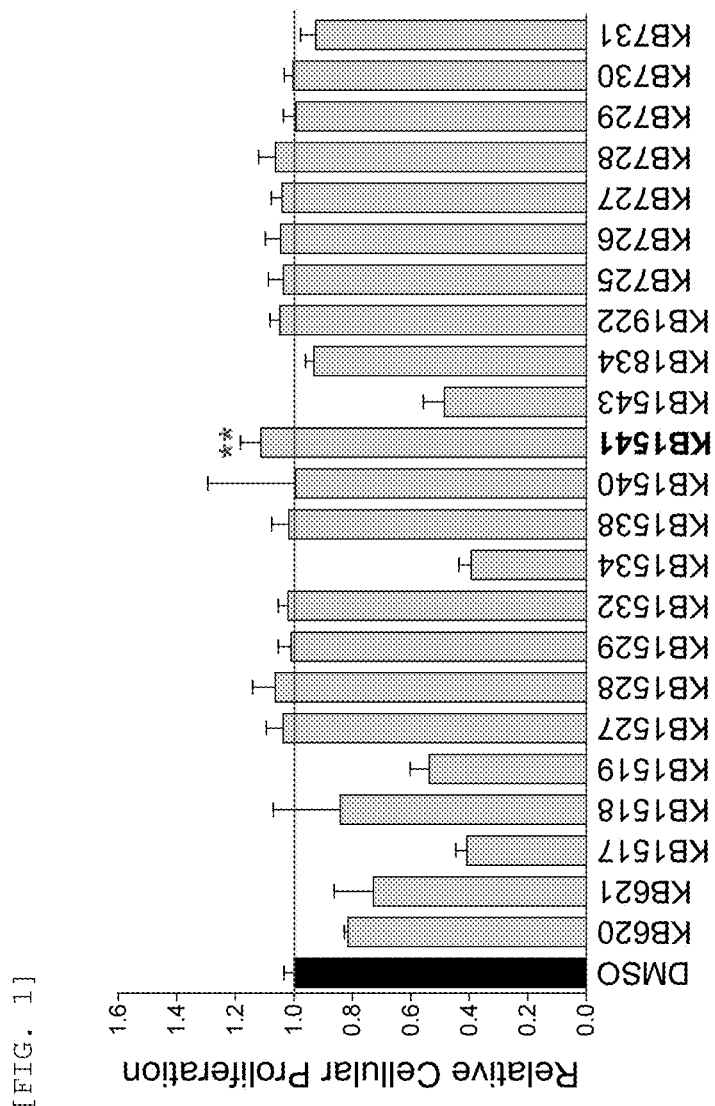

[FIG. 2]
A)
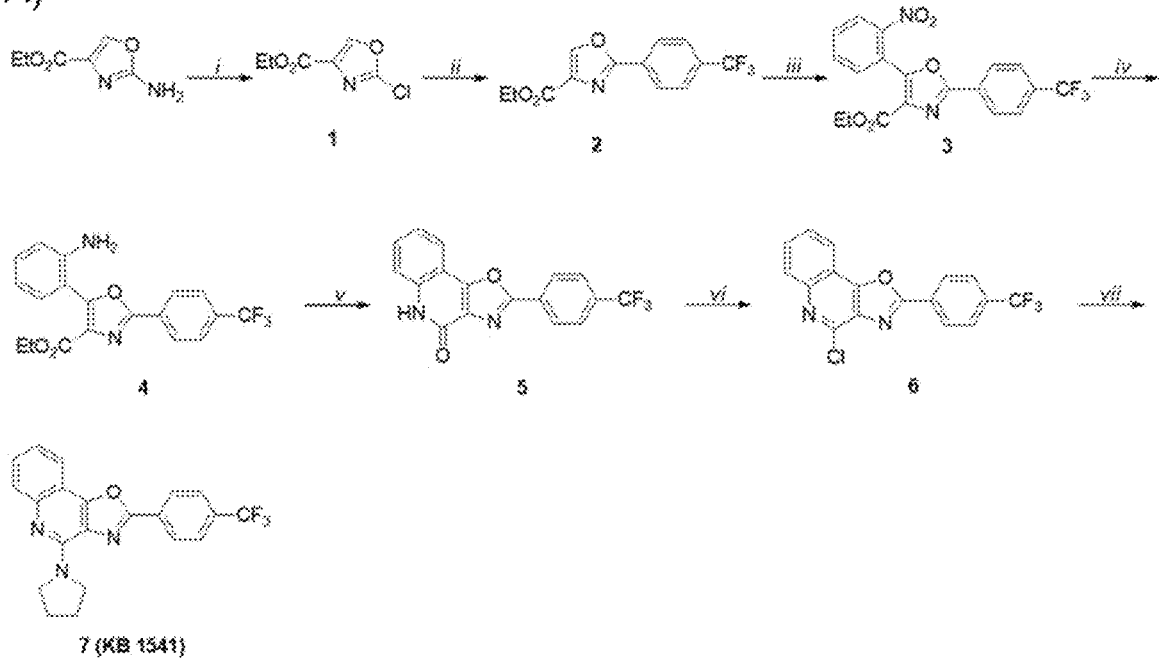
B)
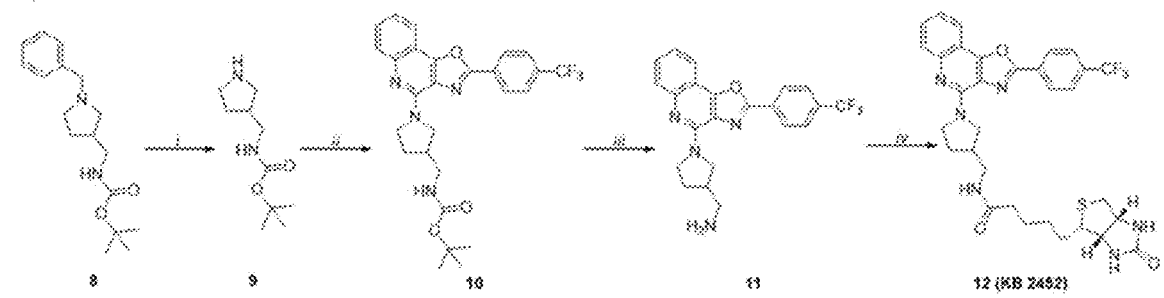

[FIG. 3]
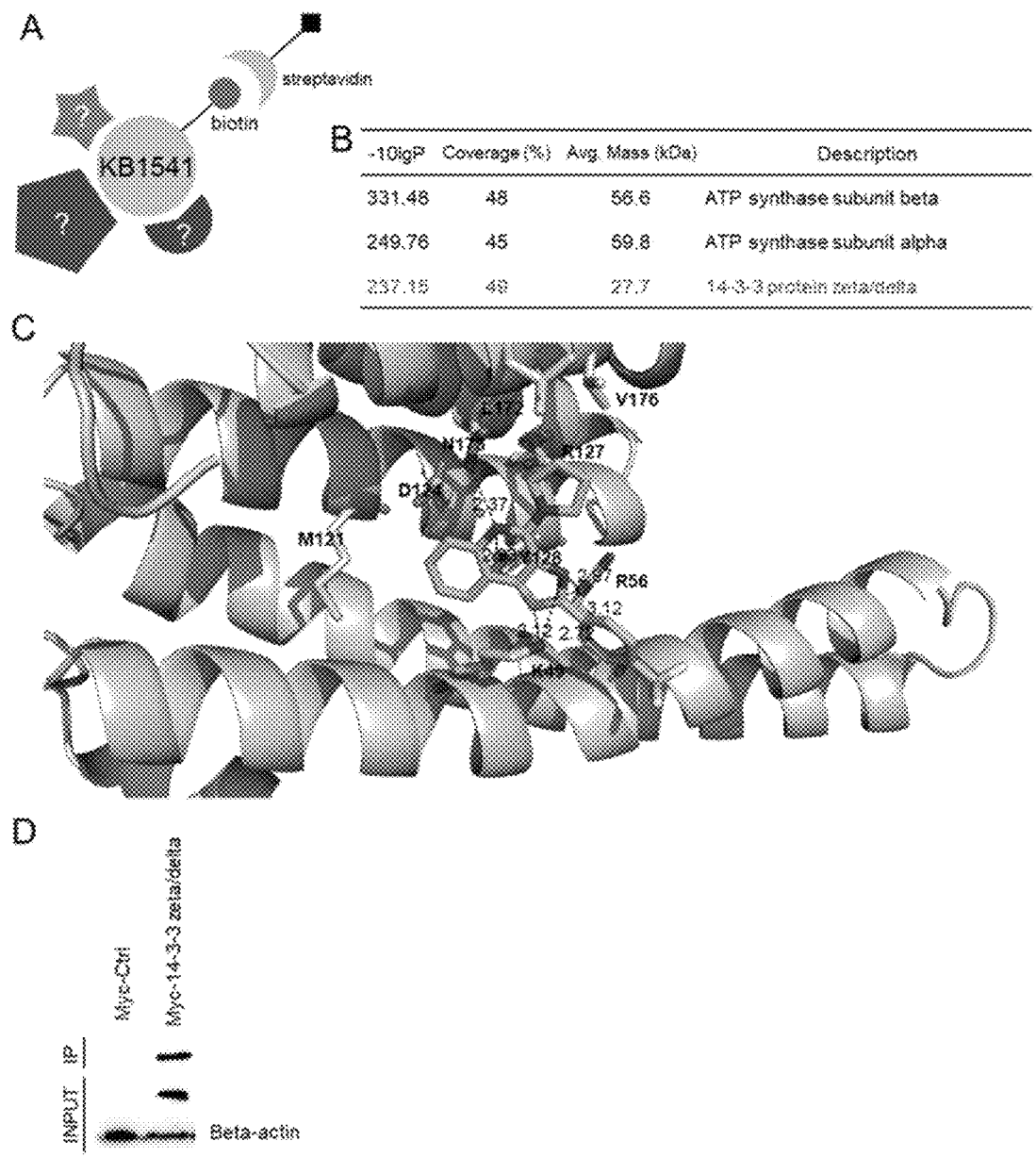

[FIG. 5]
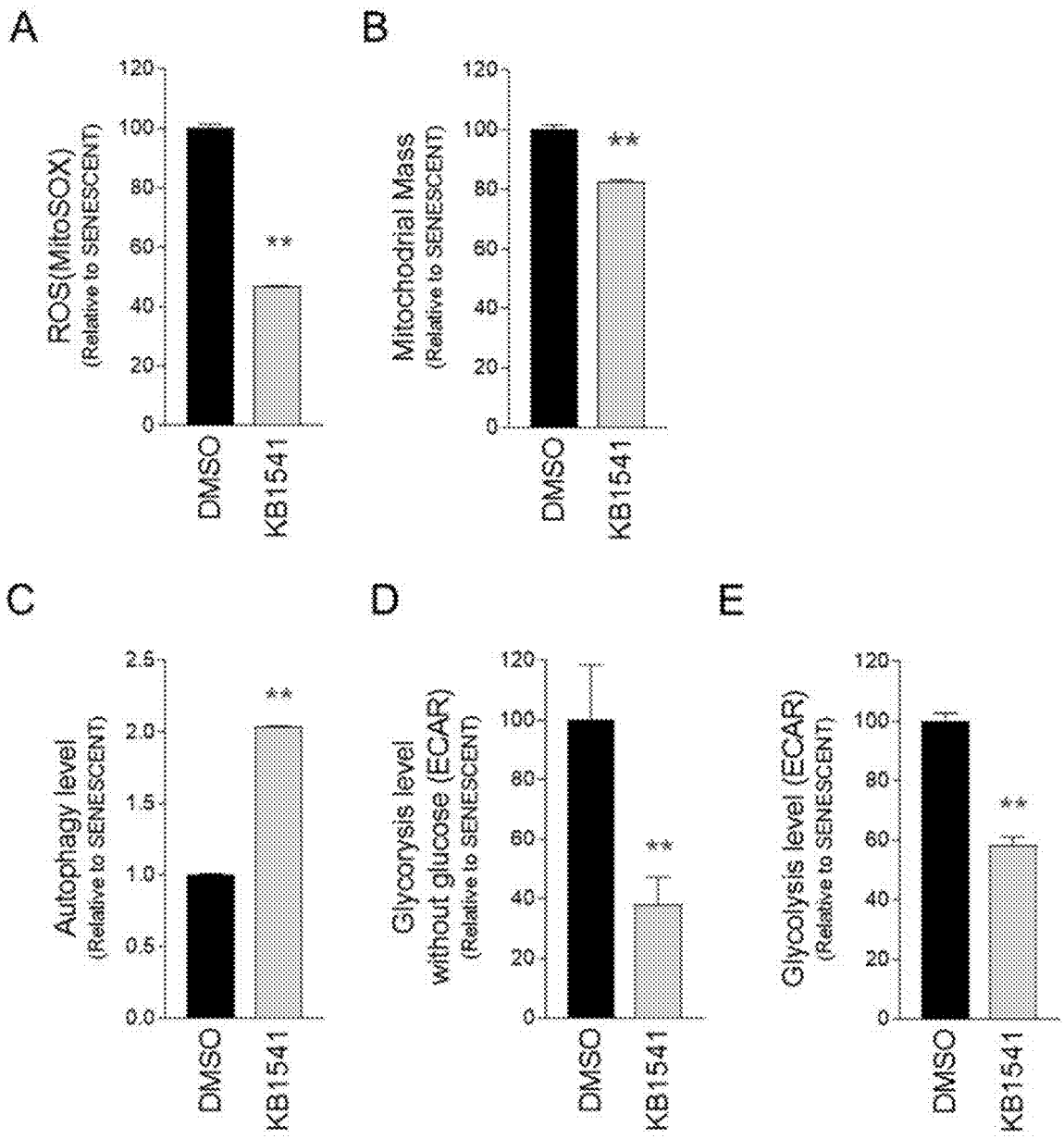

[FIG. 6]
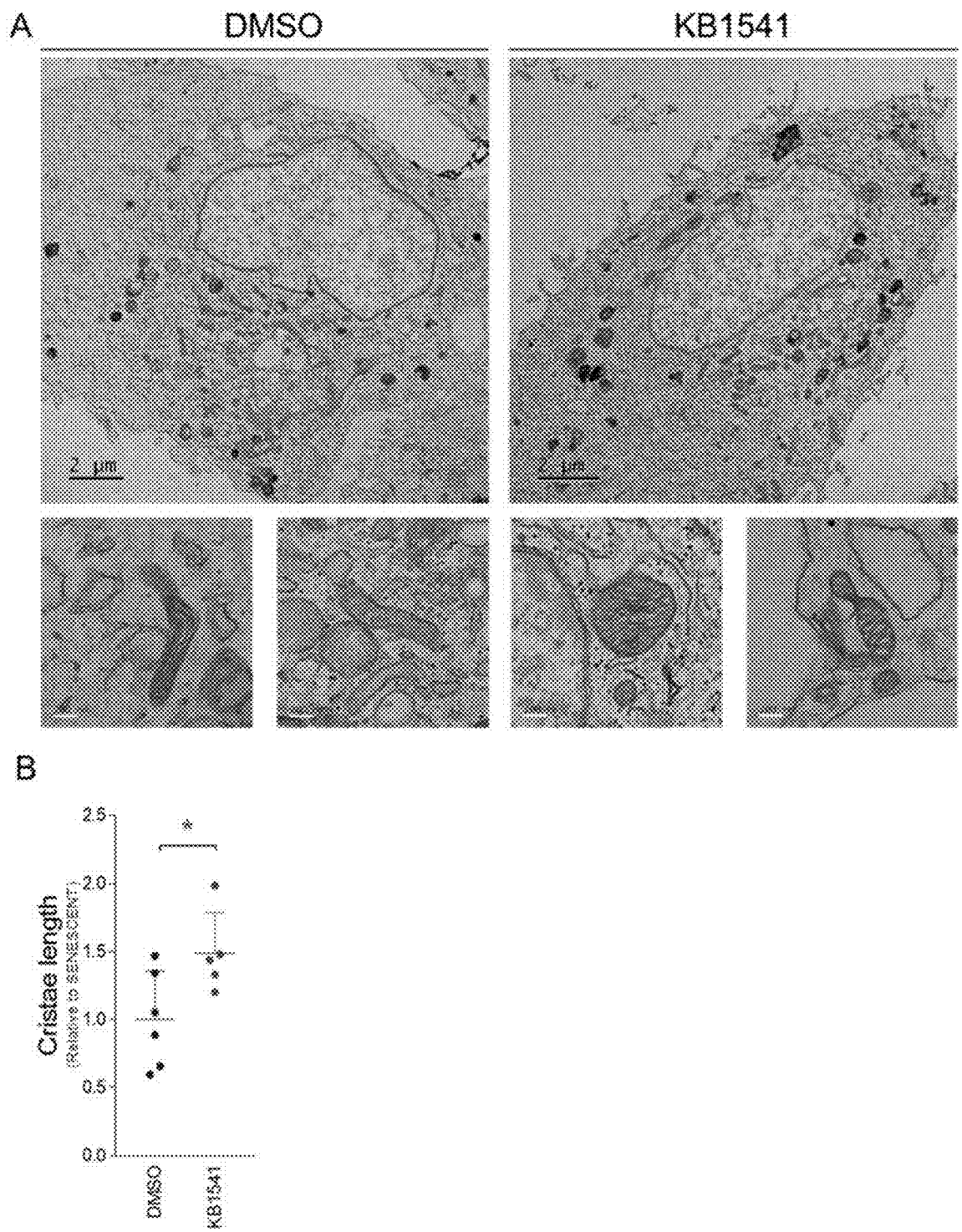

[FIG. 7]
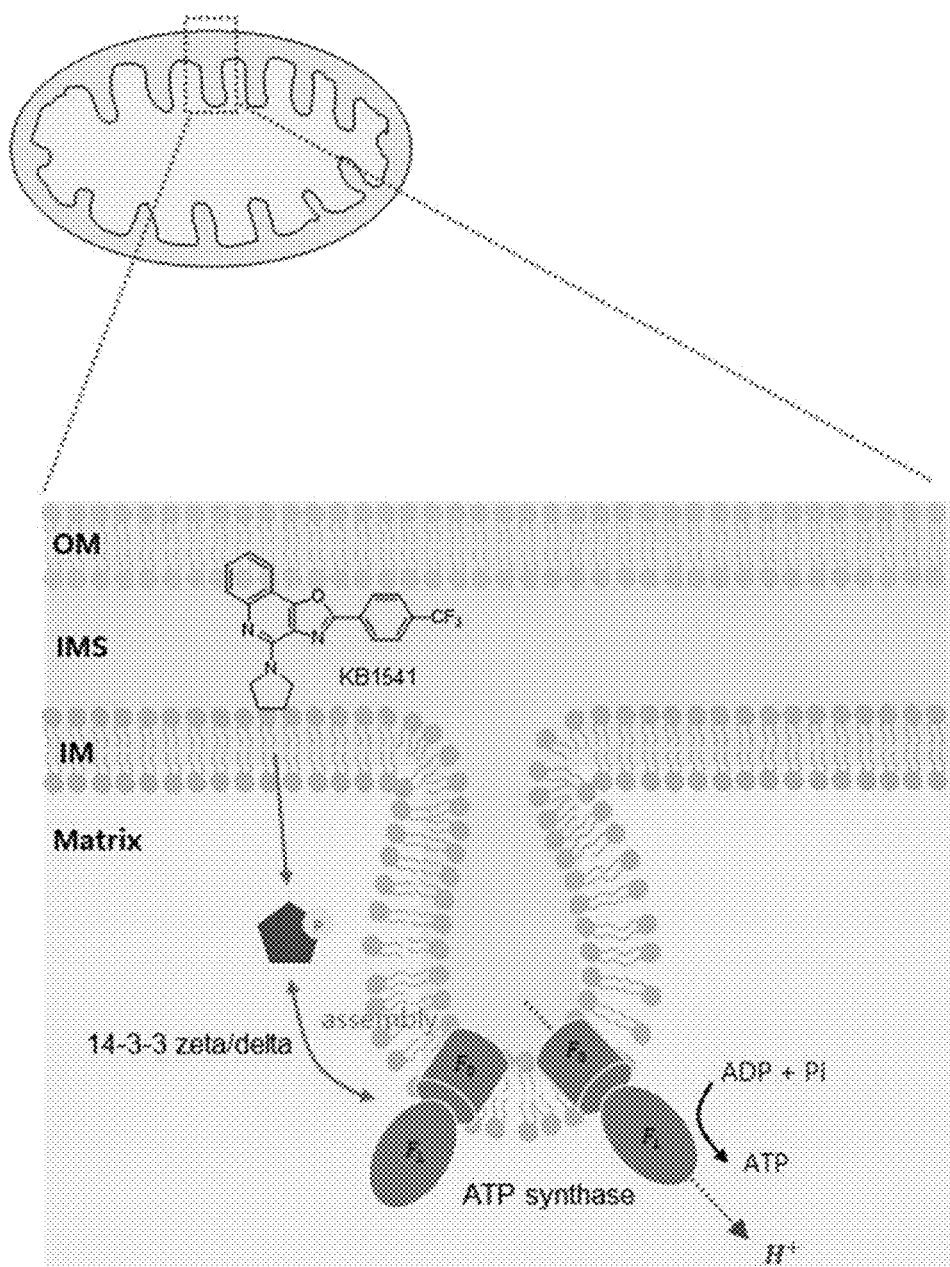

SEQUENCE LISTING

```
<160> NUMBER OF SEQ ID NOS: 9

<210> SEQ ID NO 1
<211> LENGTH: 34
<212> TYPE: DNA
<213> ORGANISM: Artificial Sequence
<220> FEATURE:
<223> OTHER INFORMATION: forward primer sequence of 14-3-3
      zeta/delta(WT)

<400> SEQUENCE: 1
agtccagtgt ggtgggatgg atammtgagc tggt                                34

<210> SEQ ID NO 2
<211> LENGTH: 35
<212> TYPE: DNA
<213> ORGANISM: Artificial Sequence
<220> FEATURE:
<223> OTHER INFORMATION: reverse primer sequence of 14-3-3
      zeta/delta(WT)

<400> SEQUENCE: 2
ggatatctgc agaatatttc ccctccttct cctgc                               35
```

<210> SEQ ID NO 3
<211> LENGTH: 35
<212> TYPE: DNA
<213> ORGANISM: Artificial Sequence
<220> FEATURE:
<223> OTHER INFORMATION: forward primer sequence of 14-3-3
      zeta/delta(S58A)

<400> SEQUENCE: 3
gcatggaggg tcgtctcaag tattgaagaa aagac                              35

<210> SEQ ID NO 4
<211> LENGTH: 35
<212> TYPE: DNA
<213> ORGANISM: Artificial Sequence
<220> FEATURE:
<223> OTHER INFORMATION: reverse primer sequence of 14-3-3
      zeta/delta(S58A)

<400> SEQUENCE: 4
gacgagcctc catgctgacc tacgggctgg tacaa                              35

<210> SEQ ID NO 5
<211> LENGTH: 10
<212> TYPE: PRT
<213> ORGANISM: Artificial Sequence
<220> FEATURE:
<223> OTHER INFORMATION: 14-3-3 zeta/delta protein

<400> SEQUENCE: 5

Val Val Gly Ala Arg Arg Ser Ser Trp Arg
1               5                   10

<210> SEQ ID NO 6
<211> LENGTH: 10
<212> TYPE: PRT
<213> ORGANISM: Artificial Sequence
<220> FEATURE:
<223> OTHER INFORMATION: 14-3-3 zeta/delta protein

<400> SEQUENCE: 6

Val Val Gly Ala Arg Arg Ser Ser Trp Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: 14-3-3 zeta/delta protein

<400> SEQUENCE: 7

Val Val Gly Ala Arg Arg Ser Ser Trp Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: 14-3-3 zeta/delta protein

<400> SEQUENCE: 8

Val Val Gly Ala Arg Arg Ser Ser Trp Arg
1               5                   10

```
<210> SEQ ID NO 9
<211> LENGTH: 10
<212> TYPE: PRT
<213> ORGANISM: Artificial Sequence
<220> FEATURE:
<223> OTHER INFORMATION: 14-3-3 zeta/delta protein

<400> SEQUENCE: 9

Val Val Gly Ala Arg Arg Ser Ser Trp Arg
1               5                   10
```

PHARMACEUTICAL COMPOSITION FOR TREATING OR PREVENTING AGING OR AGE-RELATED DISEASES

CROSS REFERENCE TO PRIOR APPLICATIONS

This application is the 35 U.S.C. 371 national stage of International application PCT/KR2021/009592 filed on Jul. 23, 2021 which claims priority to Korean Patent Application No. 10-2021-0022067 filed on Feb. 18, 2021. The entire contents of each of the above-identified applications are hereby incorporated by reference.

SEQUENCE LISTING

This application contains a Sequence Listing submitted via EFS-Web and hereby incorporated by reference in its entirety. The Sequence Listing is named SEQCRF_2440-037.txt, created on Feb. 1, 2022, and 4,096 bytes in size.

FIELD OF THE INVENTION

The present invention is relevant to a pharmaceutical composition for treating or preventing cell aging related diseases, particularly pharmaceutical composition for treating or preventing cell aging related diseases comprising a compound represented by [Chemical Formula 1] as an active ingredient.

[Chemical Formula 1]

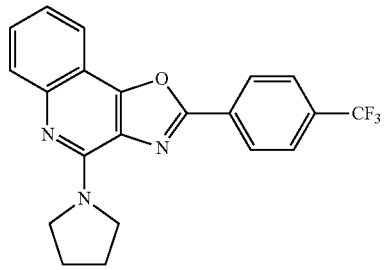

BACKGROUND OF THE INVENTION

Mitochondria theory of aging describes that the principal cause of aging or aging-related disease is the damage and malfunction of mitochondria induced by oxidative stress based on free radical hypothesis. Again, DNA mutation in somatic cells is caused by reactive oxygen species from mitochondria and thereby interferes with transcription of mitochondrial DNA and more reactive oxygen species are produced. Consequently vicious cycle is repeated and therefore aging or aging-related disease are developed. Recently, it is well elucidated that function of mitochondria is connected to arteriosclerosis, blood vessel functionality, cardiac failure, cancer, degenerative brain diseases (Parkinson's disease, Alzheimer's disease), diabetes. Therefore, it is recognized that maintenance and recovery of mitochondria is important for enhancing health and preventing disease. It is known that mitochondria play a essential role to produce cell's energy. Malfunction of mitochondria causes increased ROS, reduced ATP in electron transport chain, increased dependency on glycolysis, cell cycle suspended by energy decrease. Mitochondria has double membranes. The double membrane is composed of inner membrane and outer membrane. Proteins participating in cellular respiration concentrate on cristae of IM8. The proteins in IM of mitochondria plays a significant role to produce energy. It is well known that MICOS complex, COX 1-4 and ATP synthase is composed of IM. F1 domain in ATP synthase is an assembly of ATP synthase subunit alpha and ATP synthase subunit beta, and forms a binding domain for ADP. The formed structure transforms ADP and phosphate to ATP and thereby generate energy. It is known that 14-3-3 zeta/delta protein is an adapter protein mediating another proteins. However, more specific mechanism is not elucidated and the interaction or relationship between proteins are not unveiled yet.

PRIOR ARTS

Patents (Patent 001) Patent No. 10-2203703(KR)

DETAILED DESCRIPTION OF THE INVENTION

Problems to be Solved

The present invention aims to increase cristae in mitochondria and provide a novel composition inhibiting cell aging by forming ATP synthase.

Solution

In one embodiment of the present invention, the present invention provides a pharmaceutical composition for treating or preventing cell aging related diseases, comprising following [Chemical Formula 1] as an active ingredient:

[Chemical Formula 1]

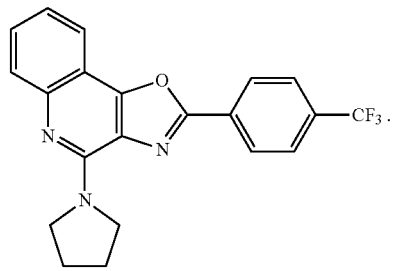

The cell aging is induced by malfunction of mitochondria.
The composition upregulates 14-3-3 zeta/delta protein.
The composition increases or forms cristae of mitochondria.
The composition activates ATP synthase.
The composition activates autophagy in a cell.
The composition reduces reactive oxygen species (ROS) in a cell.
The cell aging related diseases are selected from a group consisting of neurodegenerative diseases or disorders, cardiovascular diseases or disorders, metabolic diseases or disorders, pulmonary diseases or disorders, inflammatory or autoimmune diseases or disorders, transplant related diseases and disorders, ophthalmic diseases or disorders, proliferative diseases or disorders, chemotherapy or radiotherapy side effects, age-related diseases or disorders, fibrotic diseases or disorders, dermatological diseases or disorders, aged stem cell related diseases or disorders.

In another embodiment of the present invention, the present invention provides functional food for treating or preventing cell aging related diseases, comprising following [Chemical Formula 1] as an active ingredient:

[Chemical Formula 1]

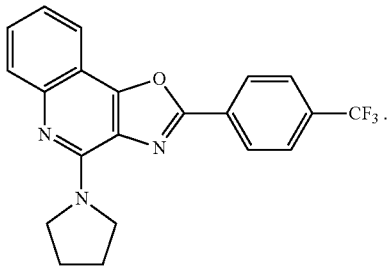

In another embodiment of the present invention, the present invention provides a cosmetic composition for treating or preventing cell aging related diseases, comprising following [Chemical Formula 1] as an active ingredient:

[Chemical Formula 1]

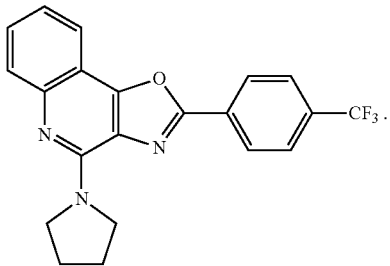

Benefits of the Invention

KB1541 in the present invention activated 14-3-3 zeta/delta protein and increased the number of ATP synthase as well as activated the ATP synthase through the activated 14-3-3 zeta/delta protein. Further, KB1541 induced the increase of the number of cristae in mitochondria and the length of the cristae. Such results were for the purpose of identifying mechanism for ATP synthase assembly as well as screening a drug candidate for recovering aging. KB1541 in the present invention is able to have a potential drug candidate for aging related diseases as well as recovering aging.

BRIEF DESCRIPTION OF THE DRAWINGS

FIG. 1 depicts the results of potential target screening for recovering senescence. Each of compounds was treated to a 96 well plate seeded with 1000 senescent cells (4 µM). After incubation for 12 days, the cells were stained with Gel green solution (1:1,000 in D.W.). Cell number was determined via fluorescence measurement using fluorescence microplate reader (excitation/emission 485 nm/535 nm).

FIG. 2 depicts a schematic diagram of synthesis of KB1541 and biotinylated KB1541.

FIG. 3 depicts the result of interaction between KB1541 and 14-3-3 zeta/delta protein. (A) a schematic diagram of IP in which biotin-connected KB1541 was used; (B) Proteins, which earned from immunoprecipitation using streptavidin magnetic beads 21 days after treated with biotinylated KB1541, were analyzed in IM-MS/MS TOF; (C) docking position of KB1541 and 14-3-3 zeta/delta protein; (D) The compound, which interacted with biotinylated KB1541 based on the result of IM-MS/MS TOF, was selected and overexpressed in HEK293T and confirmed again by immunoprecipitation.

FIG. 5 depicts the result of recovery of mitochondria based on the increased production of ATP. (A and B) Flow cytometric analysis of mitochondrial ROS and mitochondrial mass analysis using Mito tracker Green and MitoSOX; (C and D) measurement of non-glycotic glycolysis level and glycotic glycolysis level; (E) flow cytometry analysis of autophagosome level using CYTO-ID Green assay.

FIG. 6 depicts the result of mitochondria recovery induced by KB1541. (A) HDF mitochondria observed in transmission electron microscope 21 days after treated with KB1541. From left: Senescent (DMSO), Senescent (KB1541); (B) the length of cristae observed in transmission electron microscope.

FIG. 7 depicts a schematic diagram of interaction of KB1541 in mitochondria.

DETAILED DESCRIPTION OF THE INVENTION

Figure 4:
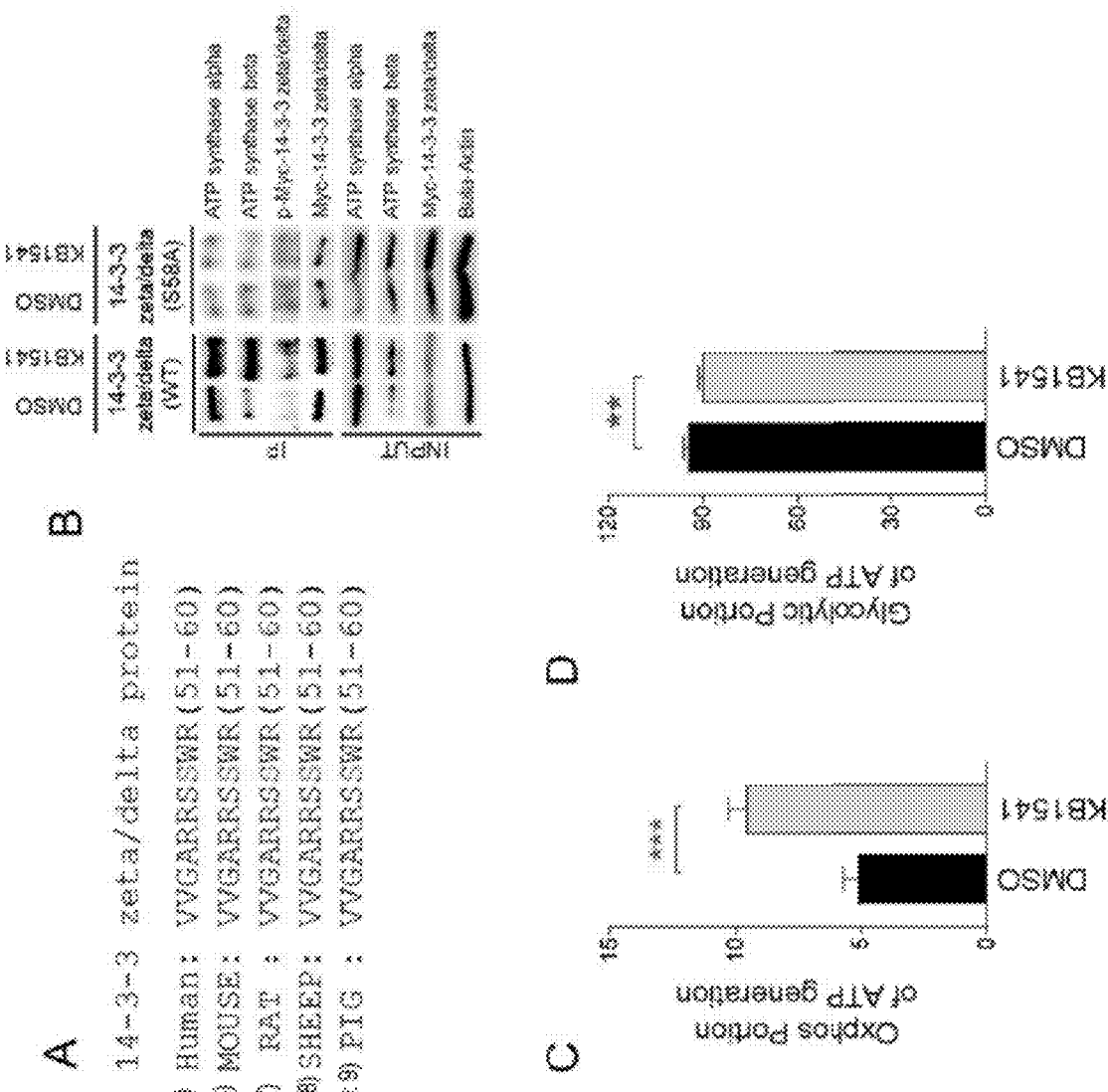
FIG. 4 depicts the result of identification of ATP synthase in a cristae-upregulated cell. (A) Conserved 58 Serine phosphorylation motif in 14-3-3 zeta/delta among across species (human, mouse, rat, sheep, pig); (B) Immunoprecipitation results of ATP synthase alpha and beta, proteins that interact with the Myc-14-3-3 zeta/delta protein transfected with HEK293T; (C and D) Glycolytic portion and oxphos portion of ATP production.

When described that a subject locates "on" the other subject in the present invention, the description includes that the subject contacts to the other subject or another subject is between the subject and the other subject.

When described that a subject "includes" an element in the present invention, the description means that the subject includes an additional element not eliminating the element unless otherwise stated.

In one aspect of the present invention, the present invention provides a pharmaceutical composition for treating or preventing cell aging related diseases, comprising following [Chemical Formula 1] as an active ingredient:

[Chemical Formula 1]

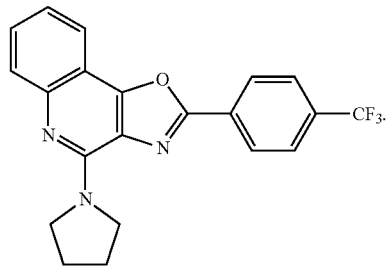

Specifically, the cell aging is induced by malfunction of mitochondria. KB1541 targeted to 14-3-3 zeta/delta protein and the 14-3-3 zeta/delta protein was activated by the KB1541. Additionally, the number and the length of cristae in mitochondria were increased.

KB1541 upregulates 14-3-3 zeta/delta protein. In other words, the KB1541 activated 14-3-3 zeta/delta protein and thereby collected alpha and beta subunit of ATP synthase, and increased the number of ATP synthase and thus activated ATP synthase. Consequently, the KB1541 induced to produce energy efficiently.

The inventors identified that when processing with KB1541, the number and the length of cristae in mitochondria were increased and ATP synthase increased and activated as well. F1 domain in ATP synthase is composed of three ATP synthase subunit alpha and three ATP synthase subunit beta, and ATP synthase is composed of an assembly of each of subunits.

It is known that 14-3-3 zeta/delta protein interacts with ATP synthase alpha and beta subunits. The inventors identified that 14-3-3 zeta/delta protein attracted ATP synthase alpha and beta subunits, and thus induced an assembly of the subunits. Particularly, phosphorylation of serine 58 residue in 14-3-3 zeta/delta protein attracted ATP synthase subunit alpha and beta, and induced ATP synthase assembly for increasing ATP synthase in mitochondria.

ATP assembly increased and thereby the efficiency in ATP production was improved considerably. The function of mitochondria as an essential function of a cell depends heavily on the efficiency in energy production. The improvement of the efficiency in energy production means recovery of malfunction of mitochondria, which in turn the function of mitochondria is recovered.

Additionally, the composition activates autophagy in a cell, and reduces reactive oxygen species (ROS) in a cell.

the cell aging related diseases are selected from a group consisting of neurodegenerative diseases or disorders, cardiovascular diseases or disorders, metabolic diseases or disorders, pulmonary diseases or disorders, inflammatory or autoimmune diseases or disorders, transplant related diseases and disorders, ophthalmic diseases or disorders, proliferative diseases or disorders, chemotherapy or radiotherapy side effects, age-related diseases or disorders, fibrotic diseases or disorders, dermatological diseases or disorders, aged stem cell related diseases or disorders, and but not limited thereto.

Examples of the neurodegenerative diseases or disorders comprise mild cognitive impairment, Alzheimer's disease/dementia, Parkinson's disease, motor neuron dysfunction and Huntington's disease.

Examples of cardiovascular diseases or disorders comprise atherosclerosis, cardiac diastolic dysfunction, aortic aneurysm, brain aneurysm, angina, arrhythmia, cardiomyopathy, congestive heart failure, coronary artery disease, myocardial infarction, endocarditis, hypertension, carotid artery disease, peripheral vascular disease, cardiac stress resistance, cardiac fibrosis, coronary thrombosis, hypercholesterolemia (hyperlipidemia, hypercholesterolemia), mitral valve prolapsed, stroke, and cerebral vascular disease.

Examples of metabolic diseases or disorders comprise diabetes, adiposis, obesity, metabolic syndrome, diabetic ulcer, insulin resistance, non-alcoholic steatohepatitis.

Examples of pulmonary diseases or disorders comprise chronic obstructive pulmonary disease, pulmonary fibrosis, idiopathic pulmonary fibrosis, emphysema, obliterating bronchiolitis, asthma, cystic fibrosis, and bronchiectasis.

Examples of inflammatory or autoimmune diseases or disorders comprise osteoarthritis, degenerative arthritis, rheumatoid arthritis, inflammatory bowel disease, oral mucositis.

Examples of ophthalmic diseases or disorders comprise macular degeneration, cataracts, glaucoma, declining vision, presbyopia.

Examples of proliferative diseases or disorders comprise various tumors and metastasis, benign prostatic hypertrophy.

Examples of chemotherapy or radiotherapy side effects comprise fatigue, malaise, low physical activity, gastrointestinal toxicity, peripheral neuropathy, hematological toxicity, hepatotoxicity, cardiotoxicity, alopecia, pain, mucositis, fluid retention, dermatological toxicity.

Examples of age-related diseases or disorders comprise osteoporosis, kyphosis, hand tremor, herniated intervertebral disc, liver disorder, renal dysfunction (renal failure, glomerulosclerosis, glomerulitis), hyposthenia, urinary incontinence, gait disorder, hair loss, hearing loss, muscular fatigue, skin conditions, skin nevus, sarcopenia, other age-related diseases induced by treatment of damaged skin and aging (i.e. smoking, hyper lipid/hyper sugar diet and disease or disorder caused by environmental elements).

Examples of fibrotic diseases or disorders comprise pulmonary fibrosis, cystic fibrosis, renal fibrosis, liver fibrosis, oral submucous fibrosis, cardiac fibrosis, and pancreatic fibrosis.

Examples of dermatological diseases or disorders comprise psoriasis, eczema, rhytides, decreased skin elasticity, pruritis, dysesthesia, papulose disorder, erythroderma, lichen planus, lichenoid dermatosis, nevi, rashes, urticaria, atopic dermatitis, eosinophilic dermatosis, reactive neutrophilic dermatosis, pemphigus, pemphigoid, immunobullous dermatosis, fibrohistocytic proliferations of skin, cutaneous lymphomas, cutaneous lupus, hyperpigmentation, scar, keloid, rosacea, vitiligo, ichthyosis vulgaris, dermatomyositis, seborrheic keratosis, blemish, freckle, melasma, actinic keratosis.

In the pharmaceutical and cosmetic composition of the present invention, the composition comprises isomer, polymorph, hydrate, solvate and all chemical types without limitation.

Additionally, a pharmaceutical acceptable salt of the composition comprises all public salt in each of compositions, for example, any organic addition salt, inorganic addition salt, metal salt or non-metal salt without limitation. More specifically, a pharmaceutical acceptable salt of desipramine includes desipramine hydrochloride, and a pharmaceutical acceptable salt of papaverine includes papaverine hydrochloride, and a pharmaceutical acceptable salt of erythromycin includes erythromycin stearate, and a pharmaceutical acceptable salt of enalapril includes enalapril maleate, and a pharmaceutical acceptable salt of ritodrine includes ritodrine hydrochloride, and a pharmaceutical acceptable salt of azlocillin includes azlocillin sodium, and a pharmaceutical acceptable salt of benazepril includes benazepril hydrochloride, and a pharmaceutical acceptable salt of mepenzolate includes mepenzolate bromide, and a pharmaceutical acceptable salt of fluphenazine includes fluphenazine hydrochloride, and a pharmaceutical acceptable salt of acetaminophen includes acetaminophen acetate, but not limited thereto.

In another aspect of the present invention, the present invention provides functional food for treating or preventing cell aging related diseases, comprising following [Chemical Formula 1] as an active ingredient:

[Chemical Formula 1]

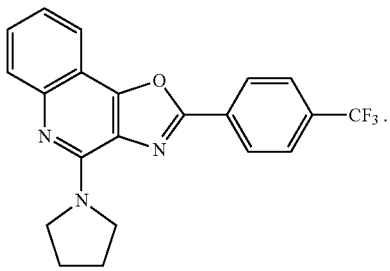

In another aspect of the present invention, the present invention provides a cosmetic composition for treating or preventing cell aging related diseases, comprising following [Chemical Formula 1] as an active ingredient:

[Chemical Formula 1]

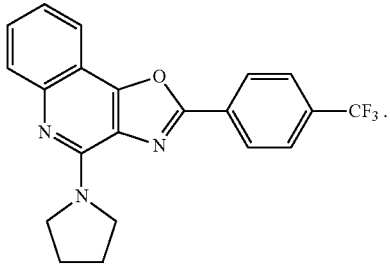

EXPERIMENTS

1. Synthesis of KB1541 and Biotinylated KB1541
(1) Synthesis of KB1541

The synthesis of KB1541 was described based on FIG. 2A. Compound 1 was synthesized from commercially available ethyl 2-aminooxazole-4-carboxylate by treating tert-butyl nitrite and copper (II) chloride in acetonitrile at 80° C. for 2 h in 64% yield. Compound 2 was obtained by reacting compound 1 with 4-(trifluoromethyl)phenylboronic acid, tetrakis(triphenylphosphine)palladium(0) and 2 M potassium carbonate solution in toluene at 80° C. for 1 h in 64% yield. Compound 3 was obtained by reacting 2 with 2-iodonitrobenzene, palladium acetate, triphenyl phosphine, and cesium carbonate in toluene at 90° C. for 3 h in 44% yield. The nitro group of compound 3 was reduced with catalytic amount of 10 wt. % palladium on activated carbon in methanol to provide compound 4. The mixture was shaken under hydrogen gas (50 psi) at room temperature for 1 h in 98% yield. Intramolecular cyclization of compound 4 was accomplished with ethylene glycol dimethyl ether (DME) and 2 M potassium carbonate solution at 90° C. for 12 h to afford compound 5 in 72% yield. Compound 6 was obtained by reacting compound 5 with phosphorus oxychloride in toluene at 120° C. for 4 h in 84% yield. Compound 7 (KB 1541) was obtained by reacting 6 with pyrrolidine at 80° C. for 3 h in 68% yield. Briefly, a total of 7 steps of reaction were carried out using ethyl 2-aminooxazole-4-carboxylate purchased from a commercial source. In order, they are Sandmeyer reaction, Suzuki reaction, Heck reaction, Hydrogenation, Cyclization, Chlorination and Alkylation.
(2) Synthesis of Biotinylated KB1541

The synthesis of biotinylated KB1541 was described based on FIG. 2B. The compound 7(KB1541) was considered as the strongest molecule of the screened compounds and thus the inventors performed pulldown assay using binding affinity between biotin and streptavidin. Protein to which compound 7 was able to bind was identified in the pulldown assay. Compound 9 was obtained through debenzylation by reacting commercially available compound 8 with 10 wt % palladium on activated carbon and catalytic amount of acetic acid in methanol. The mixture was shaken under hydrogen gas (50 psi) at room temperature for 8 h. Compound 10 was obtained by reacting 9 with compound 6 from Scheme 1 and excess amount of triethylamine (TEA) in tetrahydrofuran (THF) at 60° C. Deprotection of Boc group in compound 10 was accomplished by treating trifluoroacetic acid (TFA) in dichloromethane at room temperature for 3 h to afford compound 11. Through this reaction, we were able to obtain a compound in which a linker is conjugated to compound 7. The crude product 11 was used for the final step without further purification. Compound 12 was obtained by reacting 11 with N-succinimidyl D-biotinate, TEA in dimethylformamide (DMF) at room temperature in 53% yield.

2. Compound Screening

Senescent fibroblasts were grown in 96-well plates at a density of 1,000 cells per well. Components from the library were diluted to a final concentration of 4 μM and added to the wells every 4 days. 12 days after drug treatment, cells were washed twice with phosphate-buffered saline (PBS) and lysed in 50 μl of 0.2% SDS. The plates were incubated at 37° C. for 1 h. GelGreen® Nucleic Acid Gel Stain (150 μl) (1:1,000 in DW; 41005; Biotium, Fremont, CA, USA) was added to the wells. Cell number was determined by measuring fluorescence intensity with VICTOR Multilabel Plate Reader (2030-0050; PerkinElmer, Waltham, MA, USA). The mean and standard deviation from six replicates were determined for each of experimental groups.

3. IM-MS/MS TOF Analysis

After treating the HDF (Human diploid fibroblast) cell with biotinylated KB1541 for 14 days, immunoprecipitation was performed using streptavidin magnetic beads. The eluted proteins are subjected to IM-MS/MS (ST006; Seoul Center) sequencing and data analysis at Institute for Basic Science.

4. Plasmid Construction

The plasmid used in this experiment was constructed by amplifying it from HDF cDNA encoding human MIC60 subunit and 14-3-3 zeta/delta proteins and inserting it into the pCMV-Myc-puromycin vector (Table 1). Additionally, the 14-3-3 zeta/delta (S58A) mutant type was cloned by site-directed mutagenesis.

TABLE 1

| Vector | Primer | Sequence(5'-3') |
| --- | --- | --- |
| 14-3-3 (WT) | FWD | AGTCCAGTGTGGTGGGA TGGATAMMTGAGCTGGT |
| zeta/delta 14-3-3 | REV | GGATATCTGCAGAAtTAT TTCCCCTCCTTCTCCTGC |
| (S58A) | FWD | GCATGGAGGGTCGTCTCA AGTATTGAAGAAAAGAC |
| zeta/delta | REV | GACGAGCCTCCATGCTGA CCTACGGGCTGGTACAA |

5. Site-Directed Mutation

PCR primers were prepared using plasmid as a template vector. Two PCR primers were constructed in reverse direction including the sequence to be mutagenesis (primer sequences are in supplementary table 1). The amplified PCR product was treated with Dpn I (R0176S; New England Biolabs, Ipswich, MA, USA) for 1 h at 37° C. and purified through PCR purification. The purified PCR product was subjected to ligation using HiFi DNA Assembly Master Mix (E2621L; New England Biolabs) and transformed into DH5a Chemically Competent E. coli (CP011; Enzynomics, Daejeon, Korea).

6. Co-Immunoprecipitation pCMV-Myc-14-3-3 zeta/delta(WT) plasmid and pCMV-Myc-14-3-3 zeta/delta(S58A) plasmid were transfected with HEK293T(CRL-11268; ATCC). After transfection, selection was made in 5 µg/ml of puromycin for 14 days, and the selected cell line was treated with the drug biotinylated KB1541 at a concentration of 8 µM for 5 days. The treated cells were digested with 0.1% NP-40 cell lysis buffer to destroy cells, and IP (immunoprecipitation) of MIC60 subunit was performed using AccuNanoBeadm Streptavidin Magnetic Nanobeads (TA-1015-1; Bioneer, Daejeon, Korea). IP of 14-3-3 zeta/delta(WT) and 14-3-3 zeta/delta (S58A) were performed using anti-Myc tag antibody.

7. Measurement of Autophagic Flux

Cells were incubated in medium containing 20 µM chloroquine (CQ; C6628, Sigma-Aldrich). At 24 h after incubation, cells were further stained with Cyto-ID staining solution and 50 nM LTDR (ENZ-51031-0050; ENZO, Lausen, Switzerland) for 30 min and prepared for FACS analysis. To measure background autofluorescence, cells were incubated in medium without dye. Fluorescence from Cyto-ID was normalized with fluorescence from LTDR. Autophagic flux was calculated using the following equation: ΔMFI Cyto-ID=MFI Cyto-ID (+CQ)/MFI Cyto-ID (−CQ).

8. Measurement of Reactive Oxygen Species (ROS) and Mitochondrial Mass

For quantification of mitochondrial ROS, the cells were incubated in medium containing 5 µM MitoSOX (M36008; Life Technologies, Carlsbad, CA, USA) for 30 min at 37° C. For quantification of mitochondrial mass, the cells were incubated in medium containing 50 nM MitoTracker green (M22426; Life Technologies) for 30 min at 37° C. After staining, for the purpose of measuring mitochondrial membrane potential, cells were prepared for FACS analysis.

9. Overexpression of 14-3-3 Zeta/Delta(WT) and 14-3-3 Zeta/Delta(S58A)

The PCR fragment of 14-3-3 zeta/delta (WT) and 14-3-3 zeta/delta (S58A) were separately cloned into pCMV-Myc-puromycin. HEK293T (CRL-11268; ATCC) were transfected with Lipofectaminem 2000 Transfection Reagent (11668-019; Thermo Scientific), Selection was carried out with puromycin 3 µg/ml.

10. Seahorse Analysis

The XFe24 flux analyzer (Seahorse Bioscience XFe24 Instrument) was used according to the manufacturer's protocol. Briefly, $5\times10^4$ cells were distributed into each well of an XFe24 cell-culture plate from the XF24 FluxPak (100850-001; Seahorse Bioscience, North Billerica, MA, USA) and then cultured in a 5% $CO_2$ incubator at a temperature of 37° C. for 16 h. Next, the medium was replaced by XF Assay medium (102365-100; Seahorse Bioscience), which lacked glucose, and the cells were then cultured for another 1 h in the same incubator. The extracellular acidification rate (ECAR) was measured using an XF Glycolysis Stress Test kit (102194-100; Seahorse Bioscience). ECAR was reported in mpH/min. As a metabolic shifter, aconitase inhibitor deferiprone (379409-5G; Sigma-Aldrich) was used.

11. Measurement of Cellular ATP Levels

Cells were incubated in medium with or without 20 µM oligomycin for 24 h and then lysed with lysis buffer. ATP content was measured using a ViaLight Plus Kit (LT07-221; Lonza, Basel, Switzerland) according to the manufacturer's instructions. DNA content was measured using AccuBlue broad range dsDNA quantitation kit (31007; Biotium, Fremont, CA, USA). For measurements of relative ATP content, the luminescence of each sample was normalized to the DNA content.

<Results>

1. Chemical Screening for Compounds that Ameliorate Senescence Phenotypes

Cellular senescence is characterized by cell cycle arrest, and the inventors identified a compound recovering cell cycle arrest with additional anti-senescence effects. Screening strategies were used for identifying a compound recovering cell cycle arrest. In HTS, measurements were made 12 days after treatment in senescent HDF cells seeded at 1,000 per well with each of the 27 drugs at a concentration of 4 µM (FIG. 1). Relative cell proliferation was measured in terms of the senescent HDF. As a result of screening, the most effective compound on cell proliferation was KB541(FIG. 2A). The compound was considered effective on restoring senescence and thus used for subsequent experiments.

2. Interaction Between KB1541 and 14-3-3 Zeta/Delta Protein

The inventors hypothesized that KB151 was an effective compound on recovery of cell cycle arrest based on positive effect of KB1541 on cell proliferation (FIG. 1).

The inventors constructed biotinylated KB1541 in which biotin was attached to KB1541 for identifying how KB1541 works in cells (FIG. 2B). After the compound was treated with senescent HDF at a concentration of 4 µM, the resulting sample from IP was applied to IM-MS/MS TOF.

As a result of IM-MS/MS TOF, the interaction with 937 proteins were obtained. Among the numerous data, selected proteins were approached with a focus on the senescence and p-value and further experiments were performed (FIG. 3B).

ATP synthase alpha and beta subunits are known to be a component of ATP synthase among many proteins constituting the mitochondrial cristae. The function of the subunits is to convert ADP to ATP. It is known that 14-3-3 zeta/delta protein is an adapter protein.

The inventors hypothesized that 14-3-3 zeta/delta interaction with ATP synthase subunit alpha, beta and expected 14-3-3 zeta/delta protein to assemble ATP subunits.

Docking position of 14-3-3 zeta/delta protein to KB1541 showed a significant result (FIG. 3). Biotinylated KB1541 was treated to HEK293T transfected with 14-3-3 zeta/delta-coding gene and IP via streptavidin, and consequently the result in FIG. 3B showing interaction with biotinylated KB1541 was re-verified (FIG. 3D).

3. Mechanism for Regulating ATP Synthase Associated to 14-3-3 Zeta/Delta Protein The above results showed that KB1541 interacted with upper protein, 14-3-3 zeta/delta protein and it was anticipated that ATP synthase alpha and beta subunits composing cristae in mitochondria was influenced by 14-3-3 zeta/delta protein.

The inventors concentrated on ATP synthase an energy-producing protein that is a sub protein and is directly related to senescence. There are several types of ATP synthase and ATP locates in mitochondria cristae. The measure by which ATP synthase is produced can be seen as assembly of ATP subunit.

Therefore, the inventors studied ATP synthase alpha and beta subunits via 14-3-3 zeta/delta protein acting as an adaptor protein.

Normal proteins regulate their function through post translational modification (PTM). Phosphorylation of PTM is known as one of the important protein regulatory mechanisms. The inventors considered serine 58 residue, one of 5 phosphorylation sites of 14-3-3 zeta/delta protein, to be the PTM site linking ATP synthase alpha and beta (FIG. 4A).

Therefore, the 58th serine region of 14-3-3 zeta/delta was mutated to alanine to investigate its function. Myc-tag 14-3-3 zeta/delta(WT) vector and 14-3-3 zeta/delta(S58A) vector were transfected and overexpressed with HEK293T. Additionally, their interactions with endogenous ATP synthase alpha and beta were confirmed by IP (FIG. 4B).

As a result, ATP synthase alpha and beta proteins, which interacted with Myc-14-3-3 zeta/delta(WT) were increased KB1541 was treated to HEK293T at a concentration of 4 μM (FIG. 5B). Further, ATP synthase alpha and beta proteins, which interacted with Myc-14-3-3 zeta/delta (S58A) IP in the same way, did not change significantly when performed in the same way (FIG. 4B).

The inventors studied the changes in ATP production when assembling the ATP subunit based on the result of FIG. 4B. Oxphos portion was measured for identifying ATP resulting from oxidative phosphorylation in mitochondria cristae (FIG. 4C).

The result of oxphos portion showed that it was higher than senescent HDF when treated with KB1541. Moreover, glycolysis portion was measured for assessing the amount of ATP during glycolysis (FIG. 4D). The result showed that the glycolysis portion was reduced compared to senescent HDF (FIG. 4D).

4. Senescence Recovery Via the Overall Decrease of Senescence Markers

Senescence markers were studied for identifying the effectiveness of the compound on senescence recovery although detailed mechanism was studied.

Reactive oxygen species (ROS) was identified and measured, which damages homeostasis and metabolism of normal mitochondria. ROS increased considerably in normal senescent cells, indicating that senescence was in progress. ROS decreased in half in KB1541 treatment than senescent HDF (FIG. 5A).

The capability of removing organelles having dysfunction in senescent cells is deteriorated. Recovery of autophagy prevents accumulation of dysfunctional mitochondria and resulting in signs of senescence recovery. Mitochondrial mass and autophagy were measured for identifying the function. Mitochondrial mass decreased in HDF treated with KB1541(FIG. 5B). Moreover, autophagy level increased in HDF treated with KB1541(FIG. 5C).

Lastly, dependency of glycolysis was measured via ECAR.

Dependency of glycolysis in HDF treated with KB1541 decreased regardless of glucose like ATP study (FIGS. 5D and E).

The inventors studied level to cristae of mitochondria 12 days after senescent HDF treatment and identified senescence recovery. In mitochondria imaged by electron microscope, senescent cells had even less folds and the folds were restored as well as increased when treated with KB1541 (FIG. 6A). In graph where the images were quantified and represented, the length of cristae increased when treated with KB1541(FIG. 6B).

In summary, KB1541 in the present invention upregulated 14-3-3 zeta/delta protein and in turn the upregulated 14-3-3 zeta/delta protein formed ATP synthase (FIG. 7). At the moment, 14-3-3 zeta/delta protein joined and serine 58 residue was phosphorylated and thereby ATP synthase alpha and beta subunits were collected (FIG. 7). The formed ATP synthase produces energy efficiently and contribute to recovery of mitochondria and senescence. Therefore, in view of cell level, KB1541 is an effective candidate compound on senescence recovery.

What is claimed is:

1. A method of treating or preventing cell aging related diseases, comprising:

administering a pharmaceutical composition comprising a compound of [Chemical Formula 1] as an active ingredient to a subject:

[Chemical Formula 1]

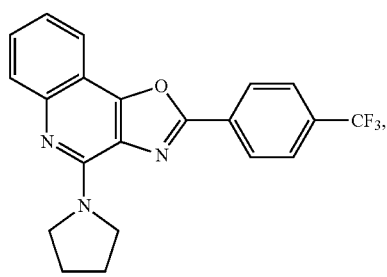

wherein the pharmaceutical composition upregulates 14-3-3 zeta/delta protein in cells, subsequently activates ATP synthase, and thereby enhances adenosine triphosphate (ATP) production and alleviating cellular senescence.

2. The method of the claim 1, wherein the cell aging is induced by malfunction of mitochondria.

3. The method of the claim 1, wherein the composition increases or forms cristae of mitochondria.

4. The method of the claim 1, wherein the composition activates autophagy in a cell.

5. The method of the claim 1, wherein the composition reduces reactive oxygen species(ROS) in a cell.

6. The method of the claim 1, wherein the cell aging related diseases are selected from a group consisting of neurodegenerative diseases or disorders, cardiovascular diseases or disorders, metabolic diseases or disorders, pulmonary diseases or disorders, inflammatory or autoimmune diseases or disorders, transplant related diseases and disorders, ophthalmic diseases or disorders, proliferative diseases or disorders, chemotherapy or radiotherapy side effects, age-related diseases or disorders, fibrotic diseases or disorders, dermatological diseases or disorders, aged stem cell related diseases or disorders.

7. A method of treating or preventing cell aging related diseases, comprising:

administering a functional food comprising a compound of [Chemical Formula 1] as an active ingredient to a subject:

[Chemical Formula 1]

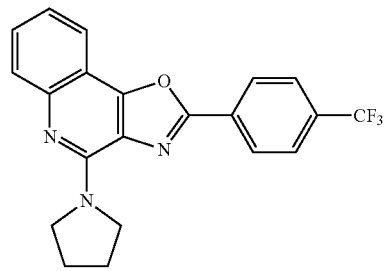

wherein the functional food composition upregulates 14-3-3 zeta/delta protein in cells, subsequently activates ATP synthase, and thereby enhances adenosine triphosphate (ATP) production and alleviating cellular senescence.

8. A method of treating or preventing cell aging related diseases, comprising:

administering a cosmetic composition comprising a compound of [Chemical Formula 1] as an active ingredient to a subject:

[Chemical Formula 1]

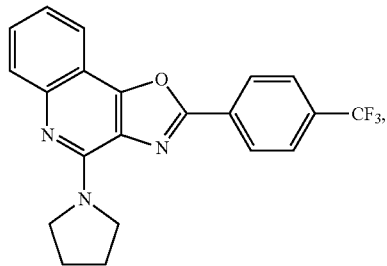

wherein the cosmetic composition upregulates 14-3-3 zeta/delta protein in cells, subsequently activates ATP synthase, and thereby enhances adenosine triphosphate (ATP) production and alleviating cellular senescence.

* * * * *